(12) United States Patent
Trissel

(10) Patent No.: US 7,312,924 B2
(45) Date of Patent: Dec. 25, 2007

(54) POLARIZING MULTIPLEXER AND METHODS FOR INTRA-ORAL SCANNING

(76) Inventor: Richard G Trissel, P.O. Box 222399, Carmel, CA (US) 93922

( * ) Notice: Subject to any disclaimer, the term of this patent is extended or adjusted under 35 U.S.C. 154(b) by 198 days.

(21) Appl. No.: 11/217,239

(22) Filed: Sep. 1, 2005

(65) Prior Publication Data

US 2007/0047079 A1    Mar. 1, 2007

(51) Int. Cl.
*G02B 27/28* (2006.01)
(52) U.S. Cl. .................. 359/497; 356/4.01; 356/602; 250/559.23; 250/559.31; 250/225
(58) Field of Classification Search ............ None
See application file for complete search history.

(56) References Cited

U.S. PATENT DOCUMENTS

| 6,364,660 | B1 | 4/2002 | Durbin et al. |
| 6,386,867 | B1 | 5/2002 | Durbin et al. |
| 6,570,659 | B2 | 5/2003 | Schmitt |
| 6,975,447 | B2 | 12/2005 | Kinoshita |
| 2004/0184038 | A1* | 9/2004 | Freischlad et al. .......... 356/512 |

\* cited by examiner

*Primary Examiner*—Arnel Lavarias

(57) ABSTRACT

A polarizing multiplexer includes a first arm with a first beam splitter to receive a first unpolarized light from an object and a first retarder coupled to the first beam splitter to generate a first right-hand circularly polarized (RHCP) beam. A normal incident beam splitter is used to receive the first RHCP beam. The multiplexer also includes a second arm with a second beam splitter to receive a second unpolarized light from an object; and a second retarder coupled to the second beam splitter to generate a left-hand circularly polarized (LHCP) beam, wherein the LHCP beam is reflected off the normal incident beam splitter and converted to a second RHCP beam. Light from both arms pass through the second retarder and are converted to p-polarized light before transmitting through the second beam splitter to an image sensor.

15 Claims, 2 Drawing Sheets

POLARIZING MULTIPLEXER AND METHODS FOR INTRA-ORAL SCANNING

This application is related to application Ser. No. 11/409,461 entitled "METHOD AND SYSTEM FOR OBTAINING HIGH RESOLUTION 3-D IMAGES OF MOVING OBJECTS BY USE OF SENSOR FUSION" filed commonly herewith and commonly owned, the content of which is incorporated by reference.

BACKGROUND

The present invention relates to intra-oral methods and apparatus for optically imaging a structure and creating representative 3D models of the structures from the images.

The dental and orthodontic field is one exemplary application of digital generation of 3D models of structures. In many dental applications, a working model of a patient's teeth is needed that faithfully reproduces the patient's teeth and other dental structures, including the jaw structure. Conventionally, a three-dimensional negative model of the teeth and other dental structures is created during an impression-taking session where one or more U-shaped trays are filled with a dental impression material. The impression tray containing the impression material, in its pliant state, is introduced into the mouth of the patient. While the tray and impression material is held in place, the material cures, and after curing, the tray and material are removed from the mouth as a unit. The impression material is allowed to solidify and form an elastic composition, which is the negative mold after removal. The working model is obtained by filling this impression with a modeling material such as dental stone in its liquid state. After being poured into the impression, the dental stone sets and hardens into a solid form which when removed from the impression is a positive representation of the structure of the patient's teeth and tissue in the jaw.

Dental patients typically experience discomfort when the dentist takes an impression of the patient's teeth. The procedure can be even more uncomfortable for the patient if the impression materials run, slump or are otherwise expelled into the patient's throat. Also, shipment and storage of the models can be costly. Hence, determination of the surface contour of teeth by non-contact optical methods and generation of digital 3D teeth models have become increasingly important.

A basic measurement principle behind collecting range data for optical methods is triangulation. Triangulation techniques are based on known geometric techniques. Given a triangle with the baseline of the triangle composed of two optical centers and the vertex of the triangle the target, the range from the target to the optical centers can be determined based on the optical center separation and the angle from the optical centers to the target.

Triangulation methods can be divided into passive and active. Passive triangulation (also known as stereo analysis) typically utilizes ambient light and both optical centers are typically camera imagers. Active triangulation uses only a single camera imager and, in place of the other camera imager, uses a source of controlled illumination (also known as structured light). Stereo analysis while conceptually simple is not widely used because of the difficulty in obtaining correspondence of object surface features between camera images. Objects with well-defined edges and corners, such as blocks, may be rather easy to obtain surface feature correspondence, but objects with smoothly varying surfaces, such as skin or tooth surfaces, with no easily identifiable surface features or points to key on, present a significant challenge for the stereo analysis approach.

To overcome the correspondence issue, active triangulation, or structured light, methods project known patterns of light onto an object to infer its shape. The simplest structured light pattern is a spot, typically produced by a laser. The geometry of the setup enables the calculation by simple trigonometry of the active triangulation sensor's range from the scanned object's surface on which the light spot falls. This computed active triangulation sensor's range to the surface of the scanned object will be referred to herein as the surface range data. Typically a sequence of images is gathered with the spot of light moved to fall across different areas of the scanned object's surface and by keeping track of where the active triangulation sensor is positioned with respect to a coordinate reference frame that is fixed with respect to the object being scanned, the sequence of active sensor surface range data can be used to construct a 3D model of the object's surface. Other patterns such as a stripe, or 2-dimensional patterns such as a grid of dots can be used to decrease the required time to capture the set of active triangulation images needed to compute the surface range data for the scanned object's surface of interest.

SUMMARY

A polarizing multiplexer includes a first arm with a first polarizing beam splitter to receive unpolarized light and a first retarder coupled to the first polarizing beam splitter to generate a first right-hand circularly polarized (RHCP) beam. A normal incident beam splitter is used to receive the first RHCP beam. The multiplexer also includes a second arm with a second polarizing beam splitter to receive unpolarized light; and a second retarder coupled to the second polarizing beam splitter to generate a left-hand circularly polarized (LHCP) beam, wherein the LHCP beam is reflected off the normal incident beam splitter and converted to a second RHCP beam before transmitting back through the second retarder, thereby being converted to linear polarization, and then transmitting through the second polarizing beam splitter.

Advantages of the above system may include one or more of the following. The system provides a compact optical configuration for combining the light from two perspectives of an object. The system can work with a system that uses Schleimpflug imaging, with a tilted object and image plane, which captures images of an object (such as a tooth), from two perspectives in order to accurately map its features using passive or active triangulation. The two perspectives are spatially combined and imaged onto a single camera imager which provides the advantage of reduced size and cost over a system using two camera imagers. Further, the configuration has the advantage of minimizing inadvertent re-illumination of the object with leakage light from the losses at the polarizing beam splitters.

When used in an intra-oral scanner, the system provides a compact intra-oral dental scanner head that enables an operator to scan a dental structure of interest with the intra oral scanner thereby accommodating a wide range of patient jaw and dentia sizes, shapes and orientations. The system automatically provides intra-oral scanning and image capturing of the scanned dental structures in the jaw through an optical aperture and combines the information available in the entire set of images obtained during the scan to create an accurate 3D model of the scanned structures. Intra-oral images of dental structures can be taken rapidly through intra-oral image apertures and with high resolution. Further, the image aperture position and orientation are known with respect to a fixed coordinate reference frame such that the acquired images can be directly processed into accurate 3D models of the imaged dental structures.

The above and other features and advantages of the present invention will be apparent in the following detailed description of the preferred embodiments of the present invention when read in conjunction with the accompanying drawings in which corresponding parts are identified by the same reference symbol.

DESCRIPTION

Figure 1:
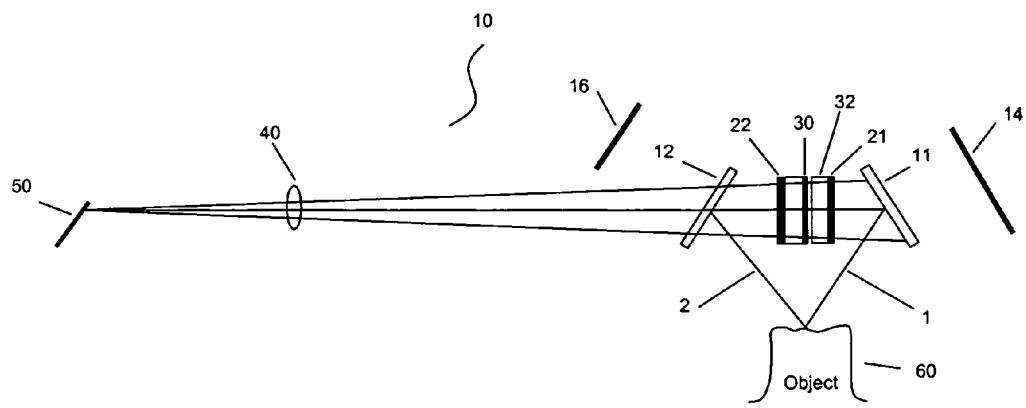
FIG. 1 shows an embodiment of a polarizing multiplexer.

FIG. 1 shows an embodiment of a polarizing multiplexer 10. In FIG. 1, arm-1 1 allows un-polarized light from an illuminated object 60 to be delivered incident on a Polarizing Beam Splitter (PBS-1) 11, which can be a Wire Grid Polarizer (WGP) or a dielectric plate polarizer or a cube polarizing beam splitter.

The WGP can be an array of thin parallel conductors supported by a dielectric substrate or a transparent substrate. When the grid spacing (g) is much shorter than the wavelength, the grid functions as a polarizer that reflects electromagnetic radiation polarized parallel ("s-polarity") to the grid, and transmits radiation of the orthogonal polarization ("p-polarity"). The WGP reflects light with its electric field vector parallel ("s-polarity") to the wires of the grid, and transmit light with its electric field vector perpendicular ("p-polarity") to the wires of the grid, but the plane of incidence may or may not be perpendicular to the wires of the grid. The WGP functions as a mirror for one polarization of light, such as the s polarity light, and is transparent for the other polarization, such as the p-polarity light.

In one embodiment, light coming from the object 60 along Arm-1 1 is split 50/50 (3 dB loss) by the PBS-1 11 with the reflected light being substantially s-polarity linearly polarized, and the transmitted light being substantially p-polarity linearly polarized. The p-polarity light transmitted through PBS-1 11 is directed to a beam dump 14 or equivalent, which serves to absorb the p-polarity light and thereby eliminates it as a potential source of interference. The s-polarity light reflected by PBS-1 11 then passes through a Quarter-Wave Retarder (QWR-1) 21 with its fast axis oriented at 45 degrees to the axis of linear polarization in a manner which results in a Right-Hand Circularly Polarized (RHCP) beam for the transmitted light exiting QWR-1 21. The RHCP light is then transmitted through the compensation window 32 and then through the normal incident Beam Splitter (B/S) 30. In this embodiment, the B/S 30 splits the light 50/50 (3 dB loss) whereby it passes 50% of the incident light with its RHCP polarization preserved while it also reflects 50% of the light, with the reflected light having its polarization changed to Left-Hand Circularly Polarized (LHCP). The LHCP light reflected by B/S 30 then passes back through the compensation window and then through the QWR-1 21 which changes the LHCP light to p-polarity linearly polarized light that continues on through the PBS-1 11 and is directed to the beam dump 14, or equivalent where the light is absorbed. The RHCP light passed by B/S 30 then passes through a Quarter-Wave Retarder (QWR-2) 22 with its fast axis oriented to result in the light passing through to exit as p-polarity linearly polarized light. This p-polarity light then efficiently transmits through a Polarizing Beam Splitter (PBS-2) 12 to a lens 40, which images the object 60 onto the camera imager 50.

In FIG. 1, arm-2 2 allows un-polarized light from the illuminated object 60 to fall incident on the Polarizing Beam Splitter (PBS-2) 12, which can be a WGP or a dielectric plate polarizer or a PBS cube. Light is split 50/50 (3 dB loss) with the reflected light being substantially s-polarity linearly polarized, and the transmitted light being substantially p-polarity linearly polarized. The p-polarity light transmitted through PBS-2 12 is directed to a beam dump 16 or equivalent, which serves to absorb the p-polarity light and thereby eliminates it as a potential source of interference. The s-polarity light reflected from PBS-2 12 then passes through the Quarter-Wave Retarder (QWR-2) 22. The retarders 22 and 21 are each comprised of a plate made of a material in which the speed of light through the material depends on the polarization of that light ("birefringent" material). The birefringent material resolves an incident light wave into a slow wave, corresponding to one component of the incident light wave's polarization vector, and a fast wave, corresponding to another, orthogonal component of that wave's polarization vector. The slow wave travels at a slower velocity, and is therefore retarded relative to the fast wave. As a result, the wave that emerges from the birefringent material can have a polarization state that differs from that of the wave incident on the material.

The light passes through the QWR-2 22 with its fast axis oriented at 45 degrees to the axis of linear polarization in a manner which results in a left-hand circularly polarized (LHCP) beam. The LHCP light continues on to the normal incident beam splitter (B/S) 30 where 50% of the light (3 dB loss) is reflected by the B/S 30 and 50% (3 dB loss) of the light passes through the beam splitter 30. The light that passes through the B/S 30 has its LHCP preserved and the LHCP light passes through the compensation window 32 and then through the QWR-1 21 that converts the LHCP light to p-polarity linearly polarized light. The p-polarity light then passes through the PBS-1 11 and is directed to the beam dump 14 or equivalent, which serves to absorb the p-polarity light and thereby eliminate it as a potential source of interference. The LHCP light that is reflected off of the B/S 30 has its polarization converted to RHCP and the RHCP light then passes through the Quarter-Wave Retarder (QWR-2) 22 resulting in p-polarity linearly polarized light. This p-polarity light then efficiently transmits through the Polarizing Beam Splitter (PBS-2) 12 to a lens 40, which images the object 60 onto camera imager 50.

The polarizing multiplexer 10 is compact in size. Further, the configuration has the advantage of not inadvertently 're-illuminating' the object with any of the leakage light from the losses at the B/S 30 and the polarizing beam splitters 11 and 12. The leakage due to the initial transmission through PBS-1 11 and PBS-2 12 simply continues on through to the beam dumps 14 and 16 or equivalent. The reflected light in arm-1 1 from the B/S 30 is LHCP due to its reflection. It is then converted to p-polarity by QWR-1 21 and transmits through PBS-1 11 to the beam dump 14 or equivalent. The transmitted light in arm-2 2 from the B/S 30 is similarly LHCP and is then converted to p-polarity by QWR-1 21, which also transmits through PBS-1 11 to the beam dump 14 or equivalent.

In one embodiment, the two arms have substantially identical optical path lengths from the object plane to the shared imaging lens 40. Since the light propagating through arm-2 2 passes through the beam splitter 30, which has a finite thickness, an equivalently thick compensating window 32 is required in the path of arm-1 1 so that the optical path lengths are matched between the two arms. Light traveling through the multiplexer incurs a 3 dB loss each way for a total of a 6 dB loss when compared with the nominal 3 dB anticipated from combining the un-polarized light from two spectrally identical objects.

Figure 2:
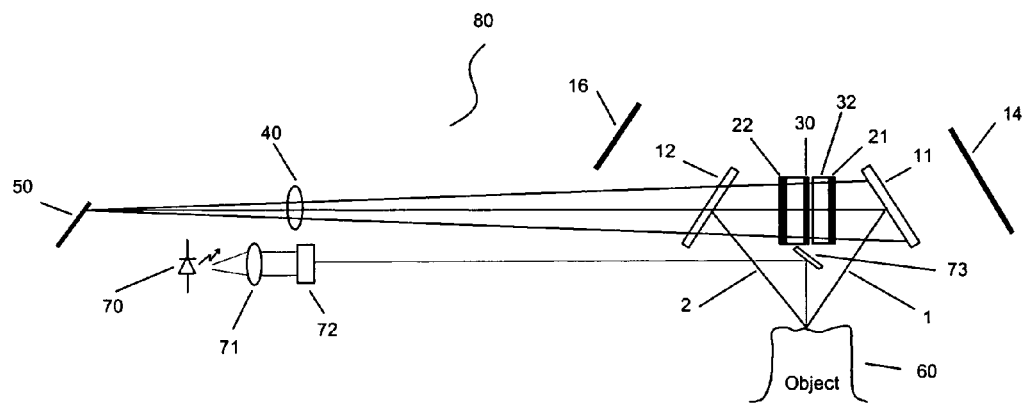
FIG. 2 shows an exemplary dental scanner head with the polarizing multiplexer of FIG. 1.

FIG. 2 shows an exemplary dental scanner head 80 that uses the polarizing multiplexer 10 shown in FIG. 1. The scanner head acquires teeth surface contour data by imaging the profile created by the intersection of a sheet of laser light with the surface of the teeth from an angle offset from the laser sheet. In one embodiment, the sensor head includes a single dental scanner head assembly which projects a laser sheet onto the teeth and then utilizes the polarizing multiplexer 10 to optically combine multiple views of the profile illuminated by the sheet of laser light. The scanner head 80 uses a laser diode 70 to create a laser beam that passes through a collimating lens 71 which is followed by a sheet generator lens 72 that converts the beam of laser light into a sheet of laser light. The sheet of laser light is reflected by the folding mirror 73 in a manner such that the sheet of laser light illuminates the surface of the tooth or other object being scanned.

In a second embodiment, the profile imaging system comprises two or more identically constructed dental scanner heads that are integrated into a common intra oral probe body. For example, in a two scanner head system one scanner head may be used to capture lingual profile images of the teeth while a second one is used to simultaneously capture buccal profile images of the teeth. Preferably, the two scanned image profiles are nominally in the same plane, although this is not a requirement for the intra-oral scanner system and the scanner may be configured such that the image profiles captured by two or more dental scanner head assemblies are in different planes. Each scanner head 80 uses the multiplexer 10 to combine a proximal and distal view of the profile illuminated by the scanner head's laser light.

Figure 3:
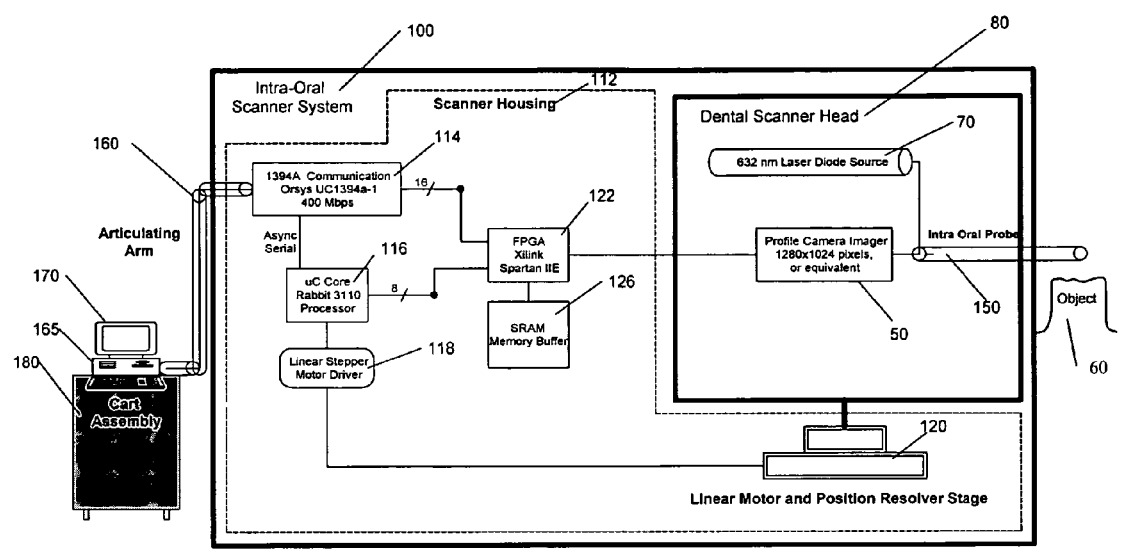
FIG. 3 shows an exemplary intra-oral scanner system with the polarizing multiplexer of FIG. 1.

Turning now to FIG. 3, an intra-oral scanner system 100 is shown. The scanner system 100 is mounted on the end of an articulating arm 160 and in one embodiment, the other end of the articulating arm 160 is attached to a cart assembly 180. The output of the scanner system 100 communicates with a computer 165 and display 170. The scanner 100 captures images through the dental scanner head 80. The camera imager 50 may be a CMOS or CCD sensor with approximately 1,280 rows and 1,024 columns of pixel elements, or equivalent. In one embodiment, the laser diode source 70 provides laser light with a wavelength of 632 nanometers. The intra-oral optical probe 150 contains the passive optical components (shown in FIG. 2) of the dental scanner head 80 such as the lens 40, 71 and 72, the PBS's 11 and 12, the QWR's 21 and 22, the beam splitter 30, the compensating window 32 and the folding mirror 73. The intra-oral optical probe 150 employs the polarizing multiplexer (not shown) to obtain views from two different perspectives of the profile of the laser illumination on the object 60 for the camera imager 50. In an alternative embodiment the laser source 70 is also packaged within the intra oral probe 150.

The scanner system 100 has a scanner housing 112 that contains a communications link such as an IEEE 1394 link 114. The link 114 communicates with a processor 116, which in turn controls a motor driver 118 that can be a linear stepper motor driver. The motor driver 118 in turn actuates a motor stage 120 to move the intra-oral end of the dental scanner head 80 across the dental structures within the intra-oral cavity. The processor 116 also communicates with custom electronics such as a field programmable gate array (FPGA)122 as well as a memory buffer 126. The gate array 122 communicates with the camera imager 50. The laser light source 70 provides light to the intra oral optical probe 150 for illumination of the dental surface being scanned.

In one embodiment, the patient's teeth are coated with a fluorescent-based coating. U.S. Pat. No. 6,592,371 titled Method and System for Imaging and Modeling A Three Dimensional Structure by Durbin et al, describes the use of a fluorescent material to coat a surface before scanning and is incorporated herein. In this embodiment, the camera imager 50 would acquire a slice of surface image data every 25 to 100 μm by using the light source 70 such as a 632 nm laser diode source to excite the fluorescent coating with a line pattern and then measuring the returned fluorescent signal as viewed from two perspectives through the polarizing multiplexer 10 contained in the intra-oral optical probe 150.

In one implementation using active triangulation to measure the surface contour of the teeth being scanned, the linear motor and position resolver stage 120 is used to move the dental scanner head along a linear path across one or more of the patient's teeth while the laser source 70 is used to illuminate the patient's teeth with a line pattern and the profile image camera 50 collects a series of profile images at a rate such that the captured surface image slices are nominally 25 to 100 μm apart. As an alternative to the laser line pattern for the active triangulation illumination, a laser light dot or a laser light two-dimensional pattern maybe be used for the active triangulation illumination.

In one embodiment of the intra oral scanner that is configured to use a single dental scanner head 80, the operator would perform the following steps to obtain an optical impression. The operator first coats one or more of the patient's teeth with a fluorescent-based coating. The operator then grasps the body of the intra-oral scanner 100, which is attached to the articulating arm 160, and positions the intra-oral optical probe 150 into the patient's oral cavity such that it is oriented to view and capture the buccal side of the coated dentition. Once the intra-oral probe 150 is properly positioned, the operator releases their hold on the body of the scanner and the articulating arm then holds the scanner 100 steady at the released position. The linear motor and position resolver stage 120, which is coupled to the dental scanner head 80, moves the dental scanner head 80 along a linear path of 5 to 100 millimeters, but typically 40 to 50 millimeters, on the buccal side of the coated dentition while the scanner system captures profile images of the observed dentition every 25 to 40 μm of linear travel. During the buccal scan, the profile image capture for the camera imager 50 is controlled by a field programmable gate array (FPGA) 122. The FPGA 122 is synchronized by the processor 116 and the FGPA performs the data compression of each image prior to transmission to the host image processor through the IEEE 1394 interface 114. Upon completion of the buccal scan, the operator would then grasp the body of the scanner 100 and reposition the intra-oral optical probe 150 to the lingual side of the coated dentition and orient the intra-oral optical probe to view the coated dentition. The operator would then release their hold on the body of the scanner and the lingual scan profile images would be captured using the same process as described above for the buccal scan. In one embodiment, a bite block incorporated into the outer shell of the housing for the intra oral optical probe 150 can be used in conjunction with the scanner system 100 to constrain and minimize the extent of relative motion between the patient's teeth and the dental scanner head 80 during a scan.

At the conclusion of the lingual scan, the buccal and lingual profile image scan data would be combined by the image processor hosted in the computer 165 to create a 3D model of the scanned teeth for display to the user on the display 170. The image processing for each frame of the profile image scan data would include level thresholding, determination of the beam center and computing the associated y and z range coordinates using active triangulation analysis. The x coordinate for each profile image scan would be obtained from the position resolver contained with the linear motor and position resolver stage 120. The range map corresponding to the surface contour of the scanned dentition would then be created by simply assigning y and z coordinates determined from the profile image with the measured x-direction value that corresponds to the instant in time that the profile image data frame was captured. The three-dimensional model generation process can include performing structured light illumination and triangulation analysis on the captured images. The system can display a representation of the three-dimensional model and transmit the three-dimensional model over a network. The three-dimensional model can be used for diagnosis and treatment of a patient.

In one embodiment, the cart assembly 180 is coupled with the scanner 100 via the articulating arm 160 extending from the cart 180. The scanner housing 112 attaches to the arm 160 through a wrist-joint interface that allows the scanner 100 to be rotated about its pitch, yaw and roll axis. The body of the housing 112 serves as a grip for the user to grasp and maneuver the scanner 100 to position the probe head 150 for a scan. The scanner 100 electrically interfaces to the cart assembly 180 through a harness running along/within the arm 160. At the start of a scan, the user releases their hold on the scanner housing 112 and the arm 160 holds the scanner system 100 steady at the released position.

The 3D model produced by the system described above can be automatically fused and displayed with other 3D images such as CT, MR or any other imaging that provides a 3D data set. Thus, if the patient's anatomy is known relative to a fixed reference, the model generated by the probe can be displayed so that it automatically correlates with an imaging database for display purposes.

It is to be understood that various terms employed in the description herein are interchangeable. Accordingly, the above description of the invention is illustrative and not limiting. Further modifications will be apparent to one of ordinary skill in the art in light of this disclosure.

The invention has been described in terms of specific examples which are illustrative only and are not to be construed as limiting. The invention may be implemented in digital electronic circuitry or in computer hardware, firmware, software, or in combinations of them.

Apparatus of the invention for controlling the equipment may be implemented in a computer program product tangibly embodied in a machine-readable storage device for execution by a computer processor; and method steps of the invention may be performed by a computer processor executing a program to perform functions of the invention by operating on input data and generating output. Suitable processors include, by way of example, both general and special purpose microprocessors. Storage devices suitable for tangibly embodying computer program instructions include all forms of non-volatile memory including, but not limited to: semiconductor memory devices such as EPROM, EEPROM, and flash devices; magnetic disks (fixed, floppy, and removable); other magnetic media such as tape; optical media such as CD-ROM disks; and magneto-optic devices. Any of the foregoing may be supplemented by, or incorporated in, specially-designed application-specific integrated circuits (ASICs) or suitably programmed field programmable gate arrays (FPGAs).

While the above embodiments have involved application of fluorescent substances to dental structures, the invention is applicable to all non-opaque and opaque surfaces. Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. An image multiplexer to combine multiple views of an object, comprising:
   a beam splitter;
   a compensation window positioned on the first side of the beam splitter; and
   first and second quarter wave retarders adjacent to the beam splitter and the compensation window; and
   a first polarizing beam splitter adapted to direct a first light beam from the object through the first quarter wave retarder, the compensation window, the beam splitter, the second quarter wave retarder, and through a second polarizing beam splitter;
   and wherein the second polarizing beam splitter is adapted to direct a second light beam from the object through the second quarter wave retarder to the beam splitter where the second light beam is reflected back through the second quarter wave retarder and through the second polarizing beam splitter.

2. The multiplexer of claim 1, comprising an image sensor to receive a multiplexed image from the first and second polarizing beam splitters.

3. The multiplexer of claim 2, comprising a lens to focus the multiplexed image onto the image sensor.

4. The multiplexer of claim 1, comprising a light generator to illuminate the object.

5. The multiplexer of claim 4, wherein the light generator comprises a laser.

6. The multiplexer of claim 1, wherein the beam splitter is a normal incidence beam splitter, and wherein the first quarter wave retarder coupled to the first polarizing beam splitter generates a first right-hand circularly polarized (RHCP) beam.

7. The multiplexer of claim 6, comprising the normal incident beam splitter to receive the first RHCP beam, and wherein the second quarter wave retarder is coupled to the normal incident beam splitter to convert the first RHCP beam to a first p-polarity beam which is than transmitted through the second polarizing beam splitter.

8. The multiplexer of claim 6, comprising the second polarizing beam splitter, and wherein the second quarter wave retarder is coupled to the second polarizing beam splitter to generate a left-hand circularly polarized (LHCP) beam, wherein the LHCP beam is reflected off the normal incident beam splitter and converted to a second RHCP beam, the second RHCP beam being passed back through the second retarder and converted to a second p-polarity beam before transmitting through the second polarizing beam splitter.

9. An intra-oral scanner system comprising:
an image multiplexer to provide multiplexed images of an object, comprising:
a beam splitter;
a compensation window positioned on the first side of the beam splitter; and
first and second quarter wave retarders adjacent to the beam splitter and the compensation window; and
a first polarizing beam splitter adapted to direct a first light beam from the object through the first ciuarter wave retarder, the compensation window, the beam splitter, the second quarter wave retarder, and through a second polarizing beam splitter;
and wherein the second polarizing beam splitter is adapted to direct a second light beam from the object through the second quarter wave retarder to the beam splitter where the second light beam is reflected back through the second quarter wave retarder and through the second polarizing beam splitter;
an image sensor to receive multiplexed images from the image multiplexer;
a lens to focus the multiplexed image onto the image sensor; and
a light generator to illuminate the object.

10. The scanner of claim 9, comprising a motor to move the image multiplexer inside an oral cavity.

11. The scanner of claim 9, comprising an image processor coupled to the image sensor to generate a three-dimensional (3D) model of the dental structure based on the images captured through the image multiplexer.

12. A polarizing multiplexer, comprising:
a first arm, including:
a first polarizing beam splitter to receive a first unpolarized light beam from an object; and
a first retarder coupled to the first polarizing beam splitter to generate a first right-hand circularly polarized (RHCP) beam;
a compensating window;
a normal incident beam splitter to receive the first RHCP beam;
a second retarder coupled to the normal incident beam splitter wherein the first RHCP beam is converted to a first p-polarity beam; and
a second polarizing beam splitter that passes the first p-polarity beam; and
a second arm, including:
the second polarizing beam splitter to receive a second unpolarized light beam from an object; and
the second retarder coupled to the second polarizing beam splitter to generate a left-hand circularly polarized (LHCP) beam, wherein the LHCP beam is reflected off the normal incident beam splitter and converted to a second RHCP beam, the second RHCP beam being passed back through the second retarder and converted to a second p-polarity beam before transmitting through the second polarizing beam splitter.

13. The polarizing multiplexer of claim 12, further comprising a lens adapted to receive the p-polarity beams.

14. The polarizing multiplexer of claim 12, further comprising an imager adapted to capture the p-polarity beams.

15. The polarizing multiplexer of claim 14, wherein the imager comprises one of: a complementary metal oxide semiconductor (CMOS) device, a charge-coupled device (CCD).

* * * * *